United States Patent [19]

Vanbraekel

[11] Patent Number: 5,715,849
[45] Date of Patent: Feb. 10, 1998

[54] PERFUME SAMPLER

[76] Inventor: Alexandre Vanbraekel, Rue de la Coquinie 230, 7700 Mouscron, Belgium

[21] Appl. No.: 858,813

[22] Filed: May 19, 1997

Related U.S. Application Data

[63] Continuation of Ser. No. 397,181, May 1, 1995, abandoned.

[30] Foreign Application Priority Data

Sep. 9, 1992 [BE] Belgium .................. 09200792

[51] Int. Cl.⁶ ........................... A45D 40/24
[52] U.S. Cl. .................. 132/314; 132/319; 401/132; 206/823; 101/129
[58] Field of Search ................... 132/314, 317, 132/318, 319; 434/377; 156/238, 241, 427; 101/129; 206/823, 581; 401/132

[56] References Cited

U.S. PATENT DOCUMENTS

| | | | |
|---|---|---|---|
| 3,494,505 | 2/1970 | Huebner et al. | 132/314 |
| 4,751,934 | 6/1988 | Moir et al. | 132/314 |
| 4,824,143 | 4/1989 | Grainger | 132/317 |
| 4,874,129 | 10/1989 | DiSapio et al. | 239/36 |
| 5,055,216 | 10/1991 | Johnson . | |
| 5,071,704 | 12/1991 | F-Ghodsian | 428/354 |
| 5,248,537 | 9/1993 | Giannavola | 428/40 |

FOREIGN PATENT DOCUMENTS 0269203 6/1988 European Pat. Off. .
0378411 7/1990 European Pat. Off. .

*Primary Examiner*—Gene Mancene
*Assistant Examiner*—PhiloGene Pedro
*Attorney, Agent, or Firm*—Birch, Stewart, Kolasch & Birch, LLP

[57] ABSTRACT

A perfume sampler comprising a perfume sample support film (1), provided for adhering to a presentation sheet (3), such as of paper, cardboard, at least one perfume sample (5), applied onto the support film (1) under the form of a gel, and a releasable protection film (6) applied on the sample, which protection film leads, upon its retraction from the support film (1), to a removal of the perfume sample (5) from the support film (1) by adhering the sample to the protection film (6) and for enabling in this way the test of the perfume by application on the skin.

12 Claims, 1 Drawing Sheet

PERFUME SAMPLER

This application is a continuation of application Ser. No. 08/397,181 filed on May 1, 1995, now abandoned.

The present invention is related to a perfume sampler, for example of the type being fixed to inside foldings, brochures, inserts of magazines, direct sale prints, sample cards, previously printed.

At the present time, several means of perfume samples exist. They comprise miniature bottles and sample tubes, having as main drawback that they are expensive, impregnated plugs in small bags and small pockets, also expensive, these small pockets and bags leading a.o. to fixing problems upon realisation of foldings, brochures, etc. Perfumed cards and foldings with a flap to detach also exist, under which flap a perfume, prepared starting from the essence under the form of a slurry, is realised by micro-encapsulation and applied in strips, the protection band releasing the scent of the perfume when it is detached. These two means does however not offer the possibility to try the perfume on the skin and, consequently, to transfer a sufficient quantity of product on the skin. The perfume can furthermore mix with the scents of ink and of paper.

The object of the present invention is to remedy above mentioned drawbacks and to provide an extremely economical perfume sampler, allowing furthermore, in conditions of absolute hygiene, the individual perfume test, the scent of which will never be altered by the used materials and the presentation support. The sampler of the invention allows also the incorporation of several perfumes.

In this respect, the sampler according to the invention comprises a perfume sample support film, provided for adhering to a presentation sheet, such as of paper, cardboard, at least one perfume sample, applied onto the support film brought under the form of a gel, and a releasable protection film applied on the sample, which protection film leads, upon its retraction from the support film, to a removal of the perfume sample from the support film by adhering the sample to said protection film and for enabling in this way the test of the perfume by application on the skin.

According to a preferred embodiment of the invention the gel comprises, besides the perfume, a viscosity increasing agent, an emulsifier, a softener, a biodegradable binder and water.

According to a particularly advantageous embodiment of the invention, the gel comprises between 1,5 and 3% of perfume, between 0,2 and 0,6% of viscosity increasing agent, between 2 and 5% of emulsifier, between 0,1 and 0,5% of softener, between 15 and 30% of biodegradable binder and the rest water, the percentages being taken with respect to the total weight of the gel.

According to another preferred embodiment, the support film is oleophobic and is of aluminium or treated polyethylene and the protection film is oleophilic and is of aluminium or treated polyethylene.

According to another particularly advantageous preferred embodiment of the invention, the protection film covers the sample support film entirely and has a larger surface than this one.

Other details and advantages of the invention will become apparent from the description of the annexed drawings to the present application, showing, by way of non limitative example, a particular embodiment of the invention.

In the two mentioned figures, the same reference numerals relate to identical or analogous elements.

Figure 1:
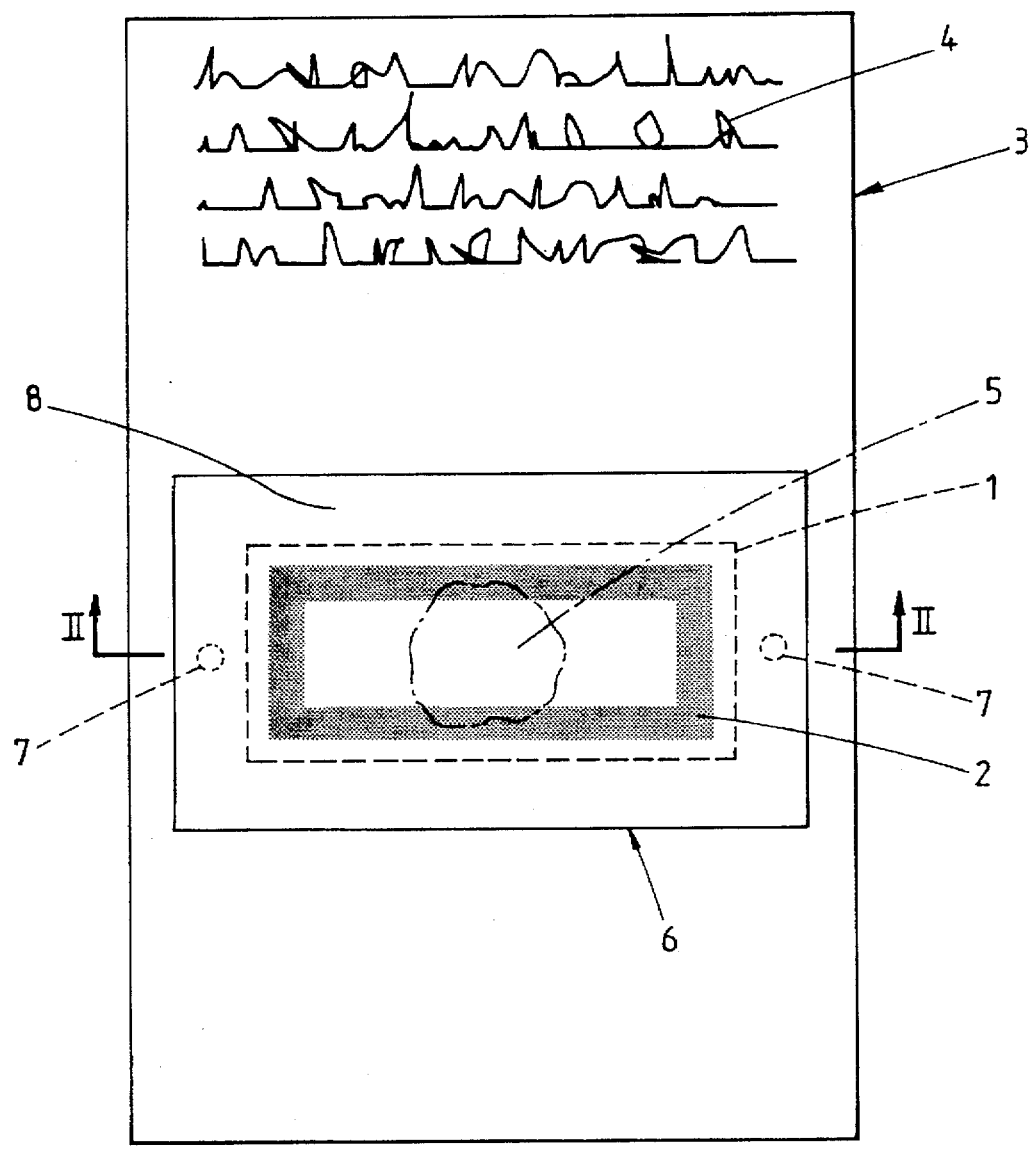
FIG. 1 is a top view of a perfume sampler of the invention.

The perfume sampler, shown in FIG. 1, comprises a perfume sample support film 1, adhering due to a small thread or band of glue 2 to a presentation sheet 3, such as of paper, cardboard or similar, comprising inscriptions 4, such as, for example, a publicity text referring to the presented perfume, a perfume sample 5 applied onto the support film 1 and a releasable protection film 6 applied onto the perfume sample 5. The perfume sample 5 is under the form of a characterising gel comprising, besides the perfume, a viscosity increasing agent, an emulsifier, a softener, a biodegradable binder and water, the gel comprising advantageously according to the invention between 1,5 and 3% of perfume, between 0,2 and 0,6% of viscosity increasing agent, between 2 and 5% of emulsifier, between 0,1 and 0,5% of softener, between 15 and 30% of biodegradable binder and the rest water, the percentages being taken with respect to the total weight of the gel. In this way, and due to the particular composition of the perfume sample under the form of gel, the protection film leads, when the releasable protection film 6 is removed from the support film 1, to removal of the perfume from the support film 1, the perfume sample 5 adhering to the protection film and allowing in this way the perfume test by application and/or slightly rubbing on the skin.

The support film 1 does not necessarily be glued to the presentation sheet 3 by means of a band or small thread of glue, its face provided for adhering to said sheet could, for example, be auto-adhesive. Advantageously, this support film is of an oleophobic material or comprises such a material, i.e. of a material refusing fats and, consecutively, essences or perfumes. A suitable material for this purpose is aluminium or polyethylene treated for this type of application. It has also to be noted that this support film can be opaque, for example white, silvered, or transparent, according to the considered application. The protection film 6 is a film, opaque or not, of a preferably larger surface than the support film 1, so as to allow easy removal from this latter film. This protection film comprises preferably an oleophilic material or is made of a material, for example aluminium or treated polyethylene, allowing the maintenance of the perfume gel on its face in contact with it. It adheres to the support or lower film 1 only by the specific consistency of the essence under the form of a gel or an emulsion. Such as just specified, upon removal of the protection or upper film 6, the entirety of the treated essence 5 separates oneself from the support or lower film 1 for adhering only to the protection film. This protection film allows in this way testing of the perfume by application on the skin. When the protection film covers the sampler support film entirely, as in the case of the represented sampler, and has a larger surface than this one, points of glue 7 are provided on the presentation sheet 3 for enabling direct adhering of the protection film 6 to this latter one, in case that a reinforcement of the adherence, essentially obtained by capillarity, would be desired between the two films. As can be seen in FIG. 1, these points of gluing 7 are situated on the presentation sheet to allow direct adheration of the edge 8 of the protection film extending beyond the support film to the presentation sheet. The films 1 and 6, and the glue lines 2 and 7 will be inodorous for not altering the perfume to be tested.

The support film 1 is not printed but the protection film 6 may be printed on its outer side, i.e. on its face which is not directly in contact with perfume sample 5. Because of this, the print is not in contact with the perfume and the skin. The protection film 6 may be cut to the desired shape, for example rectangular, such as in the considered case. In this way, it could be incorporated to a graphic concept and to the page-setting of the printed presentation sheet.

Figure 2:
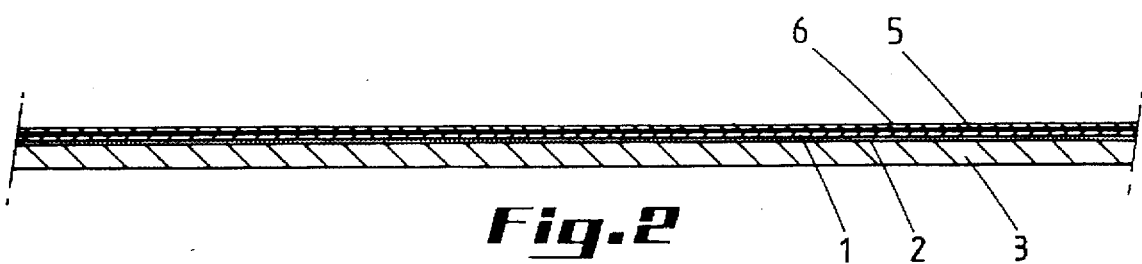
FIG. 2 is a cross section view taken along lines II—II of FIG. 1.

FIG. 2 allows to see, in a transversal cross-section, on a larger scale, the application on the presentation sheet 3, of the sampler of the invention comprising the support film 1, the perfume sample 5 and the protection film 6.

Besides the many advantages conferred by the sampler of the invention, mentioned hereinabove, it will also be noted that the perfume sample is applied without adding glue or other fixing means and that the sampler remains odourless as long as the protection film has not been detached, namely in fact that the perfume conserves all its touch and does not denature, the used films preventing evaporation and hardening of the gel. Moreover, the preparation of the gel leads to a very low consumption of essence (between 1.5 and 3% of the gel weight) in comparison with the classical samplers. Several distinctive perfume samplers, applied onto the support film, could of course also be provided, so as to permit in this way comparison of the different perfumes.

It will also be noted that, when the presentation sheet 3 comprises inscriptions or is printed, such as in the provided case, the sampler support 1 and protection 6 films may be transparent so as to permit reading of the inscriptions. However, opaque films will advantageously be used.

The perfume sampler of the invention constitutes in fact an extremely economical and easy to use sampler, and allowing to perform, in conditions of perfect hygiene, the individual test of one or more perfumes. Such as already mentioned hereinabove, several different applications could be considered inside foldings, brochures, magazines and all kinds of prints.

It is clear that the present invention is in no way limited to the above embodiments and that a lot of modifications could be applied thereto, without falling outside the scope of the present patent application.

And that is why the sampler of the invention is not necessarily limited to perfume samplers but could, of course, also be used for toilet waters and perfume waters samplers. The term "perfume" such as used in the scope of the present invention covers consequently not only perfumes, whatever their origins can be, but also toilet waters and perfume waters.

I claim:

1. A perfume sampler comprising a perfume sample support film, provided for adhering to a presentation sheet, of paper, carboard, at least one perfume sample, applied onto said support film under a form of a gel, and a releasable protection film applied on said sample, which protection film leads, upon its retraction from said support film, to a removal of said perform sample from said support film by adhering said sample to said protection film and for enabling in this way a test of a perfume by application on a skin;

wherein said protection film covers said sample support film entirely and has a larger surface than a surface of said support film; and wherein said perfume sample support film adheres by gluing to said presentation sheet.

2. A sampler according to claim 1, wherein said gel comprises, besides said perfume, a viscosity increasing agent, an emulsifier, a softener, a biodegradable binder and water.

3. A sampler according to claim 2, wherein said gel comprises between 1.5 and 3% of perfume, between 0.2 and 0,6% of viscosity increasing agent, between 2 and 5% of emulsifier, between 0,1 and 0,5% of softener, between 15 and 30% of biodegradable binder and a rest water, percentages being taken with respect to a total weight of said gel.

4. A sampler according to claim 1, wherein said support film is oleophobic.

5. A sampler according to claim 4, wherein said film is selected from the group consisting of aluminum and treated polyethylene.

6. A sampler according to claim 1, wherein said protection film is oleophilic.

7. A sampler according to claim 6, wherein said film is selected from the group consisting of aluminum and treated polyethylene.

8. A sampler according to claim 1, wherein a surface of said support film, provided for adhering to said presentation sheet, is auto-adhesive.

9. A sampler according to claim 1, wherein gluing points are provided on said presentation sheet, said points being provided for allowing to adhere an edge of said protection film extending beyond said support film.

10. A sampler according to claim 1, comprising several distinctive perfume samples applied on said support sheet.

11. A sampler according to claim 1, wherein above mentioned sample support and protection films are opaque.

12. A perfume sampler, comprising:

(1) a perfume sample support film for adhering to a presentation sheet, (2) at least one perfume sample that is in the form of a gel applied onto said support film, and (3) a releasable protection film applied onto said sample;

with the proviso that (a) said protection film leads, upon its retraction from said support film to a removal of said perfume sample from said support film—by adhering said sample to said protection film and thereby in this way enabling a test of a perfume in said perfume sample by application of said perfume to a person's skin, (b) said gel comprises, besides said perfume, a viscosity increasing agent, an emulsifier, a softener, a biodegradable binder and water, (c) said gel comprises between 1.5 and 3% of said perfume, between 0.2 and 0.6% of said viscosity increasing agent, between 2 and 5% of said emulsifier, between 0.1 and 0.5% of said softener, between 15 and 30% of said biodegradable binder, the rest of said gel consisting essentially of said water, with the recited percentages being taken with respect to a total weight of said gel, (d) said support film is oleophobic, and (e) said protection film is oleophilic.

* * * * *